Figure 1:
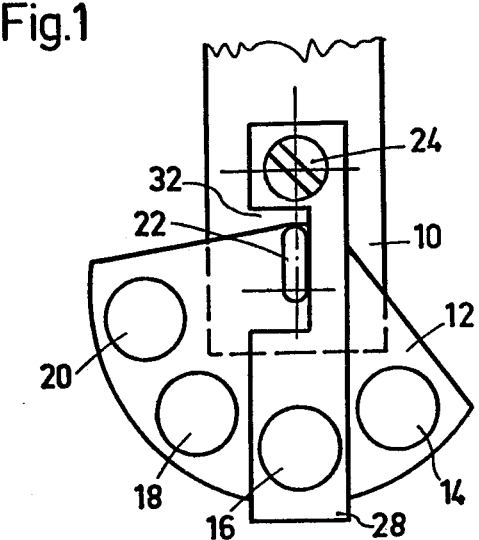

United States Patent [19]

Heine et al.

[11] 4,043,646

[45] Aug. 23, 1977

[54] FILTER MECHANISM WITH INTERCONNECTED HEAT AND COLOR FILTERS FOR OPTICAL EXAMINATION DEVICES

[75] Inventors: Helmut A. Heine; Otto H. Schmidt; Hans J. Spitschan, all of Herrsching, Germany

[73] Assignee: Propper Manufacturing Co., Inc., Long Island City, N.Y.

[21] Appl. No.: 690,423

[22] Filed: May 27, 1976

[30] Foreign Application Priority Data

Sept. 17, 1975 Germany .................... 2541503

[51] Int. Cl.² .......................... G02B 5/22; G02B 7/00; A61B 3/10; A61B 3/07
[52] U.S. Cl. .................... 350/315; 350/316; 350/318; 351/9; 351/26; 351/28; 351/29
[58] Field of Search ............. 350/315, 316, 314, 318, 350/311, 1; 351/9, 26, 28, 29; 353/55, 84; 352/148

[56] References Cited

U.S. PATENT DOCUMENTS

| | | | |
|---|---|---|---|
| 1,062,081 | 5/1913 | Converse et al. | 352/148 |
| 3,195,398 | 7/1965 | Shaw | 350/315 |

OTHER PUBLICATIONS

Wald, Josa, Mar. 1945, pp. 187–189, vol. 35, No. 3.

*Primary Examiner*—Jon W. Henry
*Attorney, Agent, or Firm*—Amster & Rothstein

[57] ABSTRACT

A filter mechanism for use with a source of white light permits selective color filtration of the white light, as well as unfiltered light transmission. A color filter support, having a plurality of spaced color filters, mounts the filters for selective movement in and out of the path of light from the source. A heat protection filter support mounts a heat protection filter for movement between an active position in the path of light from the source and an inactive position out of the path of light. In a preferred embodiment, the color filter support and heat filter support are mechanically coupled so that when a color filter is placed in the path of light, the heat filter is in its active position, but when no color filter is placed in the light path the heat filter is in its inactive position.

5 Claims, 4 Drawing Figures

U.S. Patent    Aug. 23, 1977    4,043,646

FILTER MECHANISM WITH INTERCONNECTED HEAT AND COLOR FILTERS FOR OPTICAL EXAMINATION DEVICES

This invention relates generally to optical filters, and in particular concerns a filter housing mechanism for optical examination devices.

The utilization of colored light represents a valuable supplement for diagnostic capabilities in medical examination technology. To generate the colored light, the light of an incandescent lamp is filtered with the aid of color filters which, in principle, can be inserted at an arbitrary location in the ray trajectory of the lamp. One such device, for example, is described in German Utility Pat. No. 1,987,243. Color filters for application in the medical area are generally of the type known as selective absorption filters in which the attenuation of the penetrating light radiation is dependent on its wave length. Generally speaking, there is a considerable loss of brightness when color is removed from light with such filters, and the loss increases as the bandwidth of the color filter decreases.

Other color filters are known which are based on the interference principle. Through their special characteristics, they satisfy more severe requirements with respect to their transparency characteristic. These so-called interference filters, in the simplest case, comprise a plane glass plate which has a surface layer on one or on both sides. A ray incident on this plate at a certain angle is selectively reflected. By suitably choosing the manufacturing process, filters can be produced which exhibit transparency curves having substantially steeper flanks, so that the transmitted portion of the radiation is attenuated much less than in comparable absorption filters. Light filtered in this way has greater spectral purity, and this purity can be increased to monochromaticity.

Because of their favorable characteristics, interference filters are of special interest for examining the background of the eye. They are used in this area in order to make certain phenomena better visible or, in some instances, to make invisible phenomena visible. Some phenomena are not at all visible when they are illuminated with white light and are scarcely visible when they are illuminated with light filtered through an absorption filter. Interference filters are therefore used in cases where the spectral purity or sharp bounds on the spectrum play a decisive role.

Filters used for this purpose are generally comprised of several individual filters that are cemented together, and may also include absorption filters. These combination filters are relatively expensive and have the disadvantage of low heat stability. This disadvantage results partly from the different coefficients of expansion of the individual filter glasses, and partly from the low thermal stress capacity of the surface layers. If such a filter is introduced in the ray path of a powerful lamp, the high heat radiation of the lamp creates the danger that the filter will burst as a result of thermal overload. This danger exists because it is not possible to reflect completely the unnecessary portions of the radiation. A certain fraction of the radiation is always absorbed and is thus converted into heat. As a precaution against bursting the expensive filters, a so-called heat protection filter is inserted between the light source and the color filter. This procedure is well known from film and still projectors. Since the characteristic absorption line of the heat protection filters runs quite flat, the attainment of effective heat absorption requires, as a compromise, that a portion of the visible red light must also be attenuated, so that the transmitted light has a green tinge. Such coloration is, indeed, troublesome only when it is desired to work with white light, and presents no problem when one or more color filters follow behind the heat absorption filter.

For examining the background of the eye, for example, the examiner must be able to work either with or without a color filter being inserted. In general, he begins his examination with white light, in order to orient himself on the background of the eye. In order to investigate certain phenomena in more detail, he then switches in the necessary color filter as needed. A discoloration of the white light, such as that arising from the heat protection filter that is absolutely necessary to protect the interference filter, has a disturbing effect on the examination. Under some circumstances, it can lead to erroneous findings, because portions of the background of the eye no longer proffer the accustomed color impression.

It is an object of the invention to provide a color filter housing mechanism for optical examination devices which will make it possible to insert into the light path interference filters with an optimal design, without the danger of thermal overload. It is another object of this invention that when the color filter is switched out, the interfering discoloration of the light characteristic of absorption heat protection filters be eliminated.

These objects are achieved, according to the invention, by the heat protection filter being moveable back and forth, at least, between two positions. In one of these positions the heat protection filter lies in the light path of the examination device, and in the other it lies outside the light path.

Since the heat protection filter can here be removed at will from the light path, it can be switched out of the light path for examinations under white light, and it can be switched into the light path to protect the color filter for examinations with colored light.

To facilitate operation of the device, but principally to avoid operating errors and thereby to increase the reliability of the filter arrangement, the color filter support and the heat protection filter support are preferably coupled together mechanically or electrically. This coupling is specifically arranged in such a fashion that the heat protection filter is moved out of the light path when no color filter is switched into the light path.

One embodiment, which is particularly suitable and simple from the point of view of manufacture and application, is distinguished by the fact that the color filter support is designed as a disk with openings arranged along a circular line that is concentric to the rotation axis of the disk. All but one of these openings accept one color filter each. The heat protection filter support is designed as a lever that is moveable parallel to the color filter disk.

In a specially preferred embodiment, the heat protection filter support is designed as a lever, and a cam is attached to the color filter disk. The heat protection filter support lies against this cam, and is held there under spring tension. The cam is suitably designed as a ridge standing vertically on the color filter disk and having semicircularly rounded ends. In this design, one of the semicircular ends is arranged coaxially to the rotation axis of the color filter disk.

The color filter arrangement according to the invention can be built into practically any optical examining device, for example endoscopes, otoscopes, or ophthalmoscopes. In order that the expensive color filter arrangement need not be provided for each individual device, the arrangement is preferably built into a so-called cold light projector, and in particular it is preferably built into the lamp insert of such a projector. In other words, it is built into a projector to which one or more light conducting cables are connected. This arrangement has the advantage that, even when two examination devices are connected (with the aid of a double light conducting cable), the expensive interference filter is required only once. Such a double connection is convenient for two investigators, one of whom examines the left eye and the other the right eye. With such an arrangement, the color of the light can be simultaneously changed for both observers. This examination technique is, for example, usual with fluorescence angioscopy. In this procedure, the fluorescence of a fluid injected into the blood vessels of a patient is observed under intense blue light. Such fluorescence extends into the finest branches of the blood vessels on the retina. Under some circumstances, this procedure works with different blue filters having transmission curves which differ slightly, so that certain phenomena can be made visible and can be differentiated.

As already mentioned, it makes no difference, in principle, where the color filters are switched into the light path. Of course, the thermal stress on the filters becomes less when a light conducting cable is inserted between the lamp and the filters. These cables generally have a constant course of attenuation for visible radiation and for radiation lying in the near infrared. But certain radiation components are absorbed on the background of the eye, and a large amount of energy is required to excite fluorescence. For these reasons, the light source in the cold light projector must have such high power that a heat protection filter is required even at the distal end of a light conducting cable attached to the light source, in order to protect the color filter.

Figure 2:
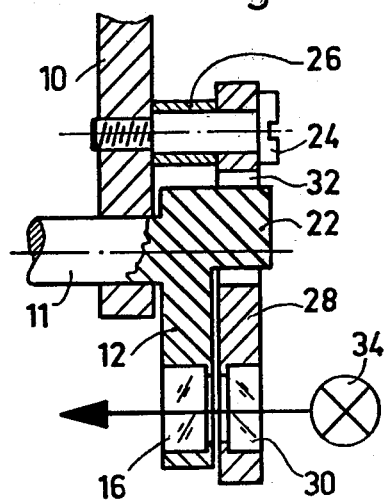

The invention will be explained in more detail below by means of the embodiments shown in the drawing. The following are shown:

FIG. 1 — a top view of a color filter arrangement;

FIG. 2 — the cross-section of the color filter arrangement of FIG. 1; and

Figure 3:
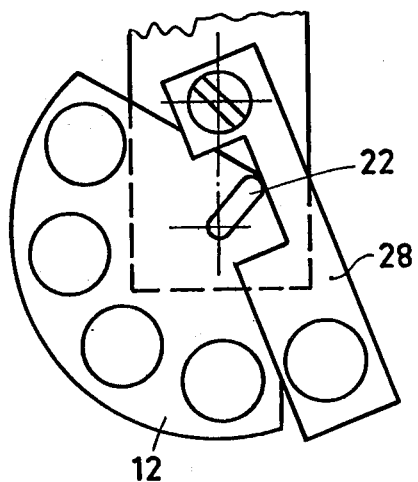

FIGS. 3 — positions of the color filter disk and the heat and 4 — protection filter support, which are different from those in FIG. 1.

According to FIGS. 1 and 2, a color filter disk 12 is mounted in a frame part 10, for example of a cold light projector, by means of a shaft 11 that is connected to a position drive (not shown). In the color filter disk 12, several openings are formed along a circle that is concentric to the shaft 11. In the present embodiment, there are four openings 14, 16, 18 and 20. Each of the openings 16, 18 and 20 has one interference color filter, while opening 14 is empty.

A ridge-shaped cam 22 is arranged on the color filter disk 12. The two ends of this cam are semicircular in shape, and one of the semicircles is coaxial with shaft 11.

A heat protection filter support 28, in the form of a lever, is mounted on support 10 by means of a screw 24 and a separation bushing 26. An opening 30 is provided in the heat protection filter support 28. This opening 30 serves to accept a heat absorption or heat reflection filter (not shown). A recess 32, which may be U-shaped, is further provided in the heat protection filter support 28. One boundary surface of recess 32 is parallel to the long axis of the heat protection filter support 28, and this boundary surface abuts the boundary surface of cam 22. A spring (not shown), acting on the heat protection filter support 28, tends to displace the heat protection filter support 28 clockwise, according to FIGS. 1, 3 and 4.

Figure 4:
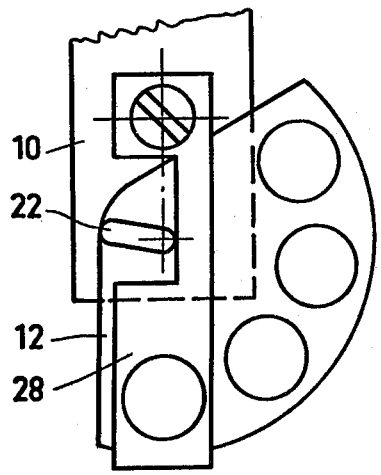

The cam 22 is arranged on the color filter disk 12 in such a fashion that, when the color filter disk is rotated counter-clockwise from the position shown in FIG. 1 to the position shown in FIG. 4, cam 22 maintains the heat protection filter support 28 in the position shown in FIGS. 1 and 4, in which the opening 30 is aligned with the incandesent lamp 34 (FIG. 2) and with one of the openings 16, 18 or 20 (FIGS. 1, 4).

When the color filter disk 12 is rotated clockwise from the position shown in FIG. 1 to the position of FIG. 3, the empty opening 14 is aligned with the incandescent lamp 34, and the color filter support 28 is moved away counter-clockwise by means of the portion of cam 22 that is eccentric with respect to shaft 11. In this way, only the opening 14, but not the heat protection filter provided in opening 30, remains in the light path.

Of course, the empty opening 14 is only necessary when it is desirable to provide in it an additional heat filter which cannot be pivoted out of the light path. Under some circumstances, the color filter disk could be cut off between openings 14 and 16, so that opening 14 would be obviated. As an alternative to this, the color filter disk 12 could be made moveable clockwise beyond the position shown in FIG. 3.

Although a specific embodiment of the invention has been disclosed for illustrative purposes, it will be appreciated by one skilled in the art that various modifications, additions, and substitutions are possible without departing from the scope and spirit of the invention.

What is claimed is:

1. A filter mechanism for use with a source of light, comprising:

at least one color filter;

first supporting means mounting said at least one color filter for movement in and out of the path of light emanating from said light source;

a heat protection filter;

second supporting means mounting said heat protection filter for movement between at least one active position in the path of light from said light source and at least one inactive position out of the path of light from said source; and interconnecting means coupling said first and second supporting means for placing said heat protection filter in said active position when one of said at least one color filter is in the path of light and placing said heat protection filter in said inactive position when none of said at least one color filter is in the path of light.

2. A filter mechanism for use with a source of light, comprising: at least one color filter; first supporting means mounting said at least one color filter for movement in and out of the path of light emanating from said light source, said first supporting means comprising a color filter receiving member mounted for rotation about a first axis positioned so that said color filter receiving member rotates in a plane intercepting said path of light; a heat protection filter; second supporting means mounting said heat protection filter for movement between at least one active position in the path of light from said light source and at least one inactive position out of the path of light from said light source; and positioning means mounted on said first supporting means controlling the position of said second supporting means for placing said heat protection filter in an active position when one of said at least one color filter is in the path of light and placing said heat protection filter in an inactive position when none of said at least one color filter is in the path of light.

3. The filter mechanism of claim 2 wherein said positioning means comprises a cam having an offset portion and said second supporting means includes a follower adapted to be engaged with said cam, so that when none of said at least one color filter is in the path of light said follower engages with said offset portion to maintain said heat protection filter out of the path of light.

4. The mechanism of claim 3 wherein said cam rotates about an axis and includes a constant radius portion and said offset portion is eccentric, engagement between said follower and said constant radius portion maintaining said heat protection filter in said path of light.

5. The mechanism of claim 2 wherein said movement of said second supporting means comprises rotation about a second axis.

* * * * *

UNITED STATES PATENT AND TRADEMARK OFFICE
CERTIFICATE OF CORRECTION

PATENT NO. : 4,043,646
DATED : August 23, 1977
INVENTOR(S) : Helmut A. Heine; Otto H. Schmidt; Hans J. Spitschan It is certified that error appears in the above-identified patent and that said Letters Patent are hereby corrected as shown below:

The assignee listed on the face of the patent should be as follows:

-- Propper Manufacturing Co., Inc., Long Island City, New York; Optotechnik Heine KG, Herrsching, Germany, Part interest each --.

Signed and Sealed this

Twenty-second Day of August 1978

[SEAL]

Attest:

RUTH C. MASON
Attesting Officer

DONALD W. BANNER
Commissioner of Patents and Trademarks